US006180769B1

(12) United States Patent
Van Kuppevelt et al.

(10) Patent No.: US 6,180,769 B1
(45) Date of Patent: Jan. 30, 2001

(54) METHOD FOR LINKING NEGATIVELY CHARGED MACROBIOMOLECULES TO PLASTICS, RESULTING LINKED COMPOSITIONS AND MICROTITRE PLATES INCORPORATING SAME

(75) Inventors: Antonius Henricus Minardus Severus Marie Van Kuppevelt, Nijmegen; Christiaan Hendrikus Adriaan Van de Lest, Zeist; Jacobus Henricus Veerkamp, Nijmegen, all of (NL)

(73) Assignee: Angiomed GmbH & Co. Medizentechnik KG, Karlsruhe (DE)

( * ) Notice: Under 35 U.S.C. 154(b), the term of this patent shall be extended for 0 days.

(21) Appl. No.: 08/860,948

(22) PCT Filed: Dec. 14, 1995

(86) PCT No.: PCT/NL95/00421
§ 371 Date: Nov. 12, 1997
§ 102(e) Date: Nov. 12, 1997

(87) PCT Pub. No.: WO96/18905
PCT Pub. Date: Jun. 20, 1996

(30) Foreign Application Priority Data

Dec. 14, 1994 (NL) .................................................. 9402122

(51) Int. Cl.[7] .................................................. C07H 21/04
(52) U.S. Cl. ...................... 536/23.1; 536/23.4; 536/23.51

(58) Field of Search ................................ 435/6; 536/23.1, 536/23.4, 23.51, 24.33, 24.3

(56) References Cited

FOREIGN PATENT DOCUMENTS 0 389 063    9/1990   (EP) .

OTHER PUBLICATIONS

Journal of Colloid and Interface Science, vol. 136, pp. 519–526, K. Yamaoka et al. "Adsorption of deoxyribonucleic acid and poly(cytidylic acid). poly(ionosinic acid) onto the poly(styrene) latex".
Journal of Colloid and Interface Science, vol. 33, No. 3, Jul. 1970, pp. 385–393, D.H. Napper "Steric stabilization and the Hofmeister Series".

*Primary Examiner*—Scott W. Houtteman
(74) *Attorney, Agent, or Firm*—Darby & Darby

(57) ABSTRACT

A method for linking strongly negatively charged biological macromolecules like deoxyribonucleic acid (DNA), ribonucleic acid (RNA) and glycosaminoglycans (GAG) to plastic substrates, comprising contacting the macromolecules and the plastics with a non chaotropic solution containing a salt in an amount of at least 20% of its saturation concentration, or having a pH below the pKa of the charged groups of the macromolecules to be linked. Also disclosed are the products of the method, in particular a microtiter plate with plastic wells coated with the negatively charged non-proteinaceous macrobiomolecules.

24 Claims, 9 Drawing Sheets

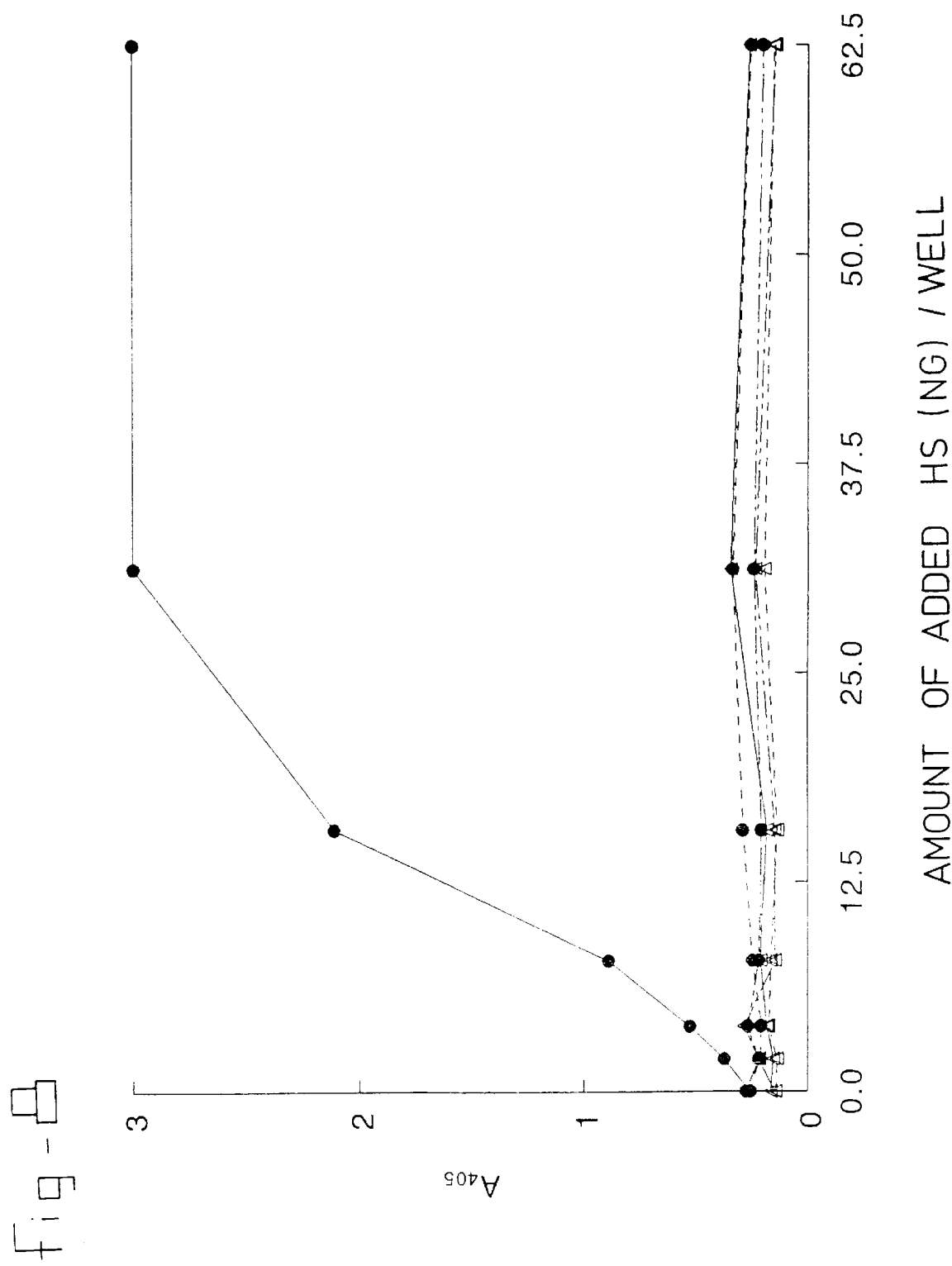

Figure 1:
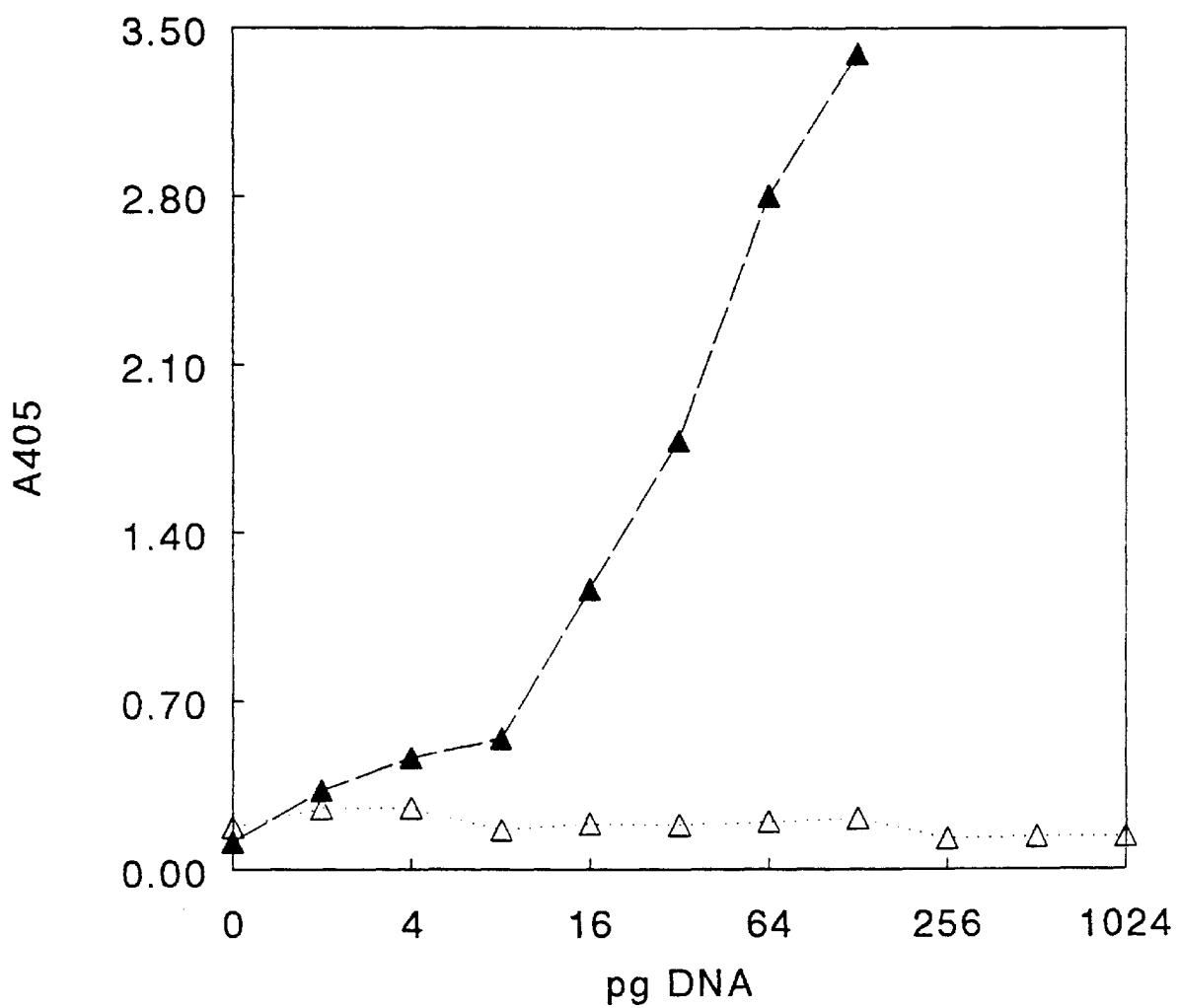

METHOD FOR LINKING NEGATIVELY CHARGED MACROBIOMOLECULES TO PLASTICS, RESULTING LINKED COMPOSITIONS AND MICROTITRE PLATES INCORPORATING SAME

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

FIELD OF THE INVENTION

The subject invention is directed at a method for preparing strongly negatively charged non-proteinaceous macrobiomolecules which are linked to plastic.

DESCRIPTION OF RELATED ART INCLUDING INFORMATION DISCLOSED UNDER 37 C.F.R. 1.97 and 1.98.

Not applicable

Strongly negatively charged biological macromolecules such as deoxyribonucleic acid (DNA), ribonucleic acid (RNA) and glycosaminoglycans (GAG) play a crucial part in cell functioning. In principal strongly negatively charged implies at least 1 negative charge per pentasaccharide of the biomolecule in so far as this is composed of pentasaccharides. DNA and RNA contain 1 negative charge per nucleotide. Glycosaminoglycans are heterogenous in this respect and can contain 1 to 4 negative charges per disaccharide. Compounds with such charge structure can be applied in the invention from which proteins, polypeptides, oligopeptides and peptides, the so-called proteinaceous molecules, are excluded. It is generally known that such proteinaceous molecules can coat polystyrene in physiological salt solutions (for example 0.15 M NaCl) however for non-proteinaceous molecules until now preferably spacer molecules have been applied.

DNA encodes all proteins, RNA is an intermediate in protein synthesis and glycosaminoglycans (such as heparin) play a part during fundamental processes such as growth, differentiation and blood coagulation. By development of molecular biological techniques nucleic acids have begun to play an increasingly large part in analysis of biological material. Fragments of DNA that are specific for example for causative organisms of disease (bacteria, viruses etc.) can be used for detection of these organisms and diagnosis of hereditary diseases also occurs at DNA level. Besides the strongly developing diagnostic importance of DNA/RNA, nucleic acids are also often applied for synthesis (also at industrial level) of specific proteins via so-called recombinant DNA techniques. Antibodies directed against nucleic acids play a part in diseases of connective tissue and autoimmune diseases such as Systemic Lupus Erythematosis. From this it is clear that good analysis possibilities of in particular DNA and RNA are of crucial importance. Microtitre plates are often used for analysis of a large number of samples. In diagnostic routine assays microbeads, tubes and strips are also used a lot. Microtitre plates are plastic plates (usually of polystyrene) which contain 96 wells in which the sample is analysed. A known example of use of such plates is for ELISA's (Enzyme Linked Immuno Sorbent Assays). A large disadvantage of these plates is that for assays wherein biological micromolecules with a strong negative charge have to be immobilized, such molecules hardly bind to the plastic plates. Immobilized macromolecule is however required for many tests. At the moment spacer molecules are used to bind negatively charged molecules to plastic. The spacer molecules bind both to the plastic and the macromolecule. Examples of such spacer molecules are protamin and polylysine, which are both positively charged proteins. Another option is the modification of DNA/RNA via biotinylation whereby it binds to avidin which can be bound in turn to plastic. Both methods require additional steps, are costly and also sensitive to disturbances. Such a disturbance is the provision of false positive results which cannot be acceptable in particular for diagnostic tests.

In Journal of Colloid and Interface Science (1990) 136: 519–526 for example Yamaoka et al describe the linkage of deoxyribonucleic acid and poly(citydyl acid.poly(inosinic acid) to poly(styrene)latex. In this procedure Yamaoka et al first dialyse the nucleic acid against the salt with which linkage is to occur. The purpose hereof is to charge the nucleic acid with the relevant ions. In the illustrated instance of page 520 replacement of monovalent $Na^+$ by divalent $Ca^{2+}$ occurs. In addition the polystyrene has to be dialysed against the relevant salt containing liquid (page 520) and thus needs pretreatment prior to linkage to the macromolecule being possible. The highest concentration of salt solution applied by Yamaoka is 0.01M and this is a concentration at which the amount of DNA more or less reaches a maximum. On page 523 it is further reported the Na-salt of DNA can hardly be linked. Yamaoka et al believe that binding of divalent anions that bind on one hand to negative groups on DNA and on the other hand to negative groups in the polystyrene is responsible for the linkage of DNA to the matrix. The divalent cation is to be regarded as a spacer molecule (page 519). The removal of the divalent cation for example with EDTA results in desorption of DNA from the matrix. The linked DNA produced by Yamaoka et al can easily be removed from the latex (p522). Obviously the DNA binding achieved with the method described by Yamaoka et al results in such weak linkage of the DNA to polystyrene that no applications with extreme circumstances such as used in hybridisation assays are possible.

In European patent Application 0.389.063 filed Sep. 26 1990 the isolation of nucleic acid via binding thereof to a solid phase in the presence of a chaotropic substance is described. KI, NaI, guadinium(iso)thio cyanate, guanidine-hydrochloride and ureum are given as examples of chaotropic substances and latex particles such as polystyrene and glycylmethacrylate particles are provided as examples of solid phase to be used. Page 4 lines 10–13 of the application illustrates that the nucleic acid is easily removed from the carrier for example by treatment with TE buffer or aqua bidest. The process described by Akzo cannot provide nucleic acid sufficiently strongly bound to solid phase to remain bound under conditions generally applicable for nucleic acid assays.

BRIEF DESCRIPTION OF THE INVENTION

The subject invention is capable of providing such linkage. The subject invention comprises a cheap, simple, efficient and reliable method to directly bind strongly negatively charged nucleic acid or glycosaminoglycan macrobiomolecules to plastic carriers such as polystyrene, polyethylene, latex, polyvinylidene difluoride or polycarbonate. These plastics need not be subjected to chemical activation or modification and can thus be applied as such which offers an appreciable advantage over the existing methods. The subject method for preparing the macrobiomolecules of the invention with strong negative charge linked to plastic is characterized in that the macrobiomolecules and plastic are contacted with each other in the presence of a non chaotropic solution capable of removing the water coat of the molecule and/or shielding the negatively charged groups of the macrobiomolecule such that direct linkage occurs between molecules and plastic i.e. without a spacer molecule and without requiring an activation step of the plastic. The linkage step is followed by removal of the solution. The conditions of the solution used depend on the applications. The method can be carried out by applying a solution with 20–100% salt saturation which provides direct linkage between molecules and plastic. Preferably a solution with a degree of saturation of more than 50% is applied, with more preference for a degree of saturation of more than 60%. The optimal results are obtained with a solution with a degree of saturation between 70–100%. The suspected mechanism of operation is as follows. The salt removes the water coat around the negatively charged molecules and shields the negative charges such that the interaction with plastic, for example polystyrene is strongly improved.

Preferably a non chaotropic salt belonging to the Hofmeister series of salts is used for the solution according to the subject invention. A non chaotropic salt of a metal from group I or II of the Periodic Table of Elements or a $NH_4^+$ salt are examples of effective salts. A solution which comprises at least a salt with an anion from the group of halogens comprising chloride and bromide, or the group phosphate, sulphate and acetate is also preferred. Of the halogens chloride is preferred. Salts that are very useful in a method according to the subject invention are NaCl, KCl, LiCl, $MgCl_2$, $MgSO_4$, $(NH_4)_2SO_4$, $NaH_2PO_4$ and $Ca(AC)_2$. A person skilled in the art will realise what salts are to be considered chaotropic and non chaotropic. In particular the ions in the Hofmeister series that tend to denature proteins $I^-$, $ClO_4^-$, $SCN^-$, $Li^+$, $Mg^{2+}$, $Ca^{2+}$ and $Ba^{2+}$ are said to be chaotropic. This list also includes the guadinium ion and nonionic urea. Generally speaking salts capable of salting out proteins are non chaotropic and salts that tend to denature proteins are chaotropic. The most chaotropic substances are salts resulting as a combination of ions from the right of the Hofmeister series and the most non chaotropic substances are combinations of ions from the left of the Hofmeister series. Combinations of any of $SO_4^{2-}$, $H_2PO_4^-$, $CH_3COO^-$ and $Cl^-$ with any of $NH_4^{30}$, $K^+$, $Cs^+$, $Na^+$ are non chaotropic salts. In general chaotropic agents increase the solubility of nonpolar substances in water. Any agent capable of illustrating the increase in solubility of a nonpolar substance in water to the same degree as salts from the left of the Hofmeister series as mentioned above can be considered suitable for carrying out the invention if they do not denature the macrobiomolecule. LiCl is an example of a suitable salt.

In particular $(NH_4)_2SO_4$ is superior as a non chaotropic salt in the process according to the invention because only low amounts of the compound to be bound are required for optimal binding. In general the method according to the subject invention will be carried out with a salt capable of salting out proteins. The pH is not critical for the method when salt is applied. The correct circumstances will vary per biomolecule and a person skilled in the art will know for biomolecules such as RNA, DNA which pH and which salt concentrations are applicable.

The method according to the invention can also be carried out by using a solution of the macrobiomolecule with a lower pH than the pKa of the charged groups of the macrobiomolecule to be linked whereby direct linkage occurs between the molecule and the plastic without a spacer molecule. By selection of an extremely low pH, for example pH 0 (i.e. 1 M HCl) negative groups (phosphate groups in DNA/RNA, sulphate groups in GAG) will become neutral whereby linkage will be strongly simplified. If the method is carried out at a very low pH this will mean in general that the pH is lower than 2. Of course a combination of the two above-mentioned embodiments (variation of salt concentration and pH) of the method is possible.

DETAILED DESCRIPTION OF THE INVENTION

The method according to the subject invention can be carried out in the various embodiments mentioned above at a temperature between 0–100° C., preferably between 2–90° C. Good results are achieved at both 4° C. and 80° C. The higher the temperature the quicker the coating will proceed. At 80° C. very efficient coating can be achieved. The temperature to be used will not only depend on the period of time in which coating is required but will possibly be dependent on the type of molecule with which the coating is carried out. Double stranded DNA will denature at higher temperatures which can be undesirable. The method according to the subject invention can be carried out with a linkage step lasting at least 5 to 10 minutes, for example 10 minutes at a temperature of 80° C. The method according to the invention can also be carried out overnight at 4° C. with good results or for 1 hour at 80° C. with very good results. The period of time is also dependent on the time required for any steps optionally to be carried out after the coating for example with antibodies and detection reagents.

The method according to the subject invention preferably comprises one or more steps after the linkage step for removing the linkage solution. The linked product can be rinsed with water to achieve this. It is also possible to apply salt solution buffered with Tris with Tween® 20 for example 0.1% Tween®. In general one will rinse with a product that is not detrimental to the linked biomacromolecule. In practice rinsing with at least two rinsing steps with water and once with salt solution buffered with Tris with 0.1% Tween® suffices well. A person skilled in the art will understand which solutions can be applied.

For hybridisation research double stranded DNA can be linked using the method according to the subject invention. The method for linkage of double stranded DNA to plastic according to the invention proceeds best in a saturated salt solution in water. A solution of NaCl is excellent. A saturated solution of NaCl contains approximately 5 M NaCl, depending on the temperature of the solution. Good results can be achieved for the linkage step with incubation overnight at 4° C. After the linkage the DNA can subsequently be rendered single stranded thereby becoming suitable for hybridisations. After rinsing the linked double stranded DNA can be rendered single stranded by addition of 0.2 M NaOH/0.2 mM EDTA for 5 minutes at room temperature. The linked nucleic acid is attached in such a manner to the plastic that it will not be released during the usual steps required for hybridisation tests. In particular nucleic acid linked to plastic according to the invention will exhibit a linkage strength sufficiently high for it to remain substantially linked to the plastic after treatment for 10 minutes at 56° C. with an aqueous EDTA solution of more than 1 mM. It will preferably be resistant to treatment with an aqueous EDTA solution of more than 10 mM. Treatment under the same temperature and period of time with solutions of more than 100 mM and even up to 200 mM are possible with the coated plastic obtainable with the process according to the invention. Thus a plastic substance coated in a simple manner with nucleic acid which is sufficiently strongly bound to remain bound under hybridisation conditions has been provided by the invention.

Probably the nucleic acid attaches to the plastic via the phosphate sugar groups. The bases are thereby left available for the hybridisation test (base-pairing). Obviously carrying out amplification reactions such as PCR belongs to the possibilities.

The subject method can also be applied extremely well for linking glycosaminoglycans. For linking glycosaminoglycans one can operate very efficiently solely by applying a salt solution as described above, preferably a substantially saturated salt solution. The method however proceeds more efficiently upon combination of saturated salt conditions with an acid pH, preferably pH 0. The method can also be carried out at 4° C. but also at higher temperatures even up to 80° C.

The method in any of the embodiments disclosed above is applicable for any test wherein negatively charged nucleic acid or glycosaminoglycan macrobiomolecules are involved that need to be immobilised. One can think here of assays with DNA, RNA and GAG. Modified forms of such molecules also fall within the group of biomolecules that can be applied. One of the more important areas of application lies in diagnostic methods in which DNA/RNA are involved, in particular for detecting pathogenic organisms with the aid of specific DNA probes by means of hybridisation techniques. In addition the diagnosis of diseases in which anti DNA or anti RNA or anti GAG antibodies are involved is another possible embodiment. Above all the biological characteristics of GAG can be well used in this manner. The HIV virus for example binds specifically to heparan sulphate (a GAG) and therefore microtitre plates coated with heparan sulphate according to the subject method can be used for detection of the HIV virus, thereby providing a very suitable AIDS test.

The subject method provides an extremely simple and cheap method for linkage of the biomolecules of the invention to plastic. It is possible to produce plastic carriers, for example microtitre plates with material linked thereto which can be maintained for a long time and in a dried form. A long time implies a period of a number of months but possibly also a number of years. Tests have been carried out with microtitre plates coated with a glycosaminoglycan such as heparan sulphate and stored in a dry form for 2 months at 4° C. The coated microtitre plates maintained their capacity to react with specific antibodies after this period of time. The linked molecules above all remain bioactive, i.e. can still bind specific antibodies and undergo hybridisation tests because the binding places required therefore are not involved in the linkage to plastic. Furthermore with the subject method a very strong binding to plastic is obtained which is so strong that hybridisation tests with the concomitant many rinsing steps and optional heating steps are possible. Any plastic coated with a negatively charged macrobiomolecule according to the invention without the presence of a spacer molecule exhibiting a binding strength such that it is resistant to treatment with a 1 mM aqueous EDTA solution at 56° C. for 10 minutes falls within the scope of the invention. By resistant to treatment it is implied that a substantial amount of the macrobiomolecule remains attached to the plastic after the treatment with EDTA.

A further advantage of tests with such material according to the invention is that lower background values are obtained which is important in work with unpurified sera. In particular this is important for blood research. In the subject method sufficient material is linked to render tests extremely sensitive. As a further advantage it can be mentioned that material with which the plastic is coated is compatible with every detection system that is current such as by means of radio activity, enzyme markers, fluorescent markers and chemo luminescent markers. An additional advantage is that in particular upon application of nucleic acid like RNA, DNA and GAG's the enzymes that usually degrade such substrates (RNAse, DNAse and glycosidases) are not active. In particular for RNA applications this is extremely interesting because these tests are usually very sensitive to RNA degradation.

A number of embodiments of tests that have been carried out applying the subject invention are described below.

EXAMPLE 1

Binding of Double Stranded DNA to Polystyrene Microtitre Plates

This example is directed at coating double stranded DNA using different circumstances (FIG. 1). A pGEM vector either labelled with digoxigenin or non-labelled with an insert of FABP-cDNA (Fatty Acid Binding Protein=FABP) was contacted with the polystyrene wells of microtitre plates. Every well contained 100 $\mu$l of water saturated with NaCl. The linkage reaction was carried out overnight at 4° C. After rinsing 3 times with $H_2O$ and once with salt solution buffered with Tris with 0.1% Tween® the wells were incubated with a solution of 100 $\mu$l anti digoxygenin antibody conjugated to alkaline phosphatase. Bound antibody was made visible by use of p nitrophenyl phosphate as substrate. No difference was found between application of saturated NaCl in water or 1 M HCl.

FIG. 1 illustrates a curve for binding of double stranded DNA to polystyrene microtitre plates. The X axis reveals the number of picograms of DNA set out against the absorption measured at 405 nm on the Y axis. The interrupted dashed line with dark triangles indicates labelled DNA with saturated NaCl and the dotted line with light triangles indicates non-labelled DNA with saturated NaCl.

EXAMPLE 2

Hybridisation of DNA Under Different Circumstances

Figure 2:
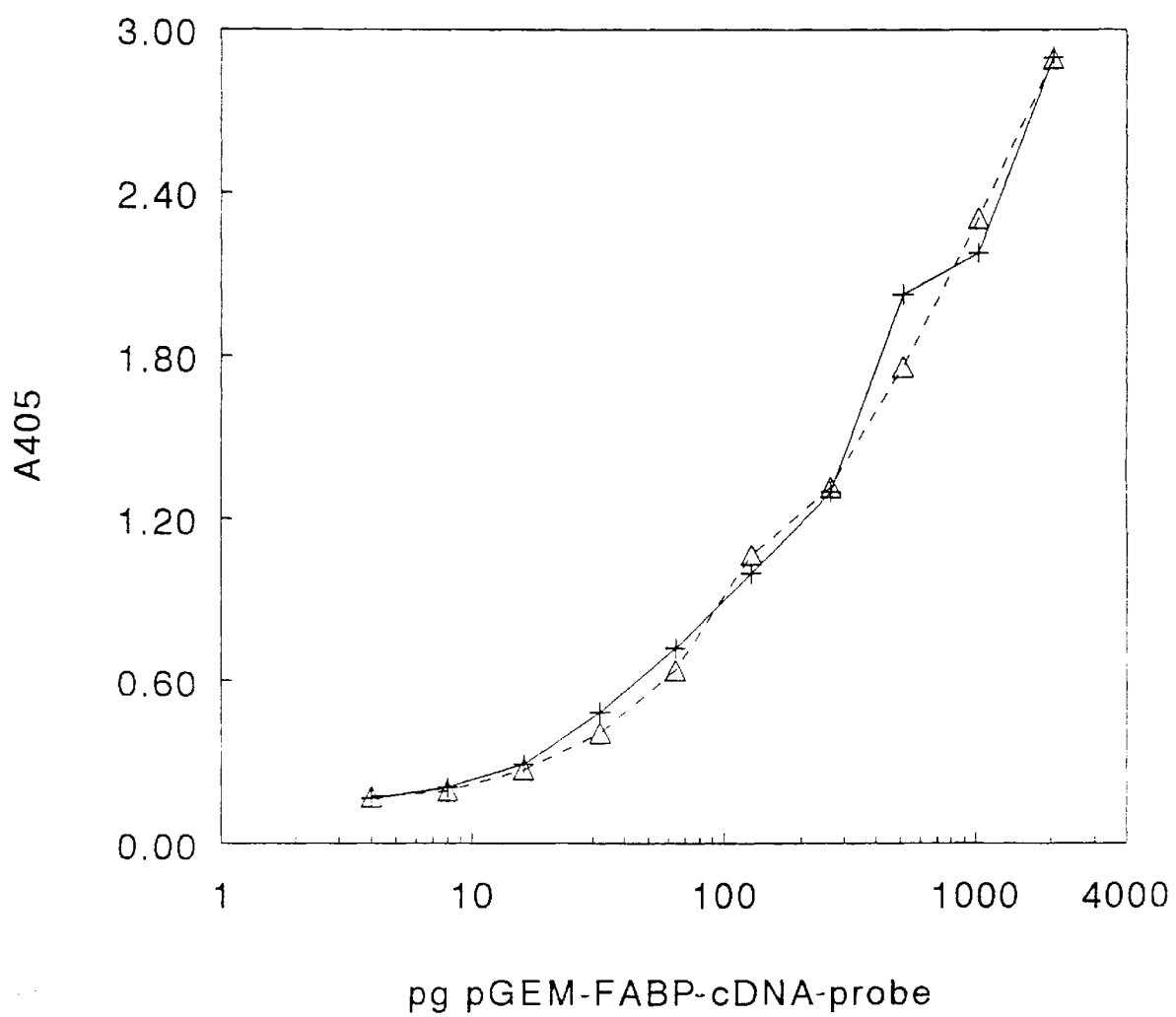

The results of these hybridisations are illustrated in FIG. 2. pGEM vector with FABP-cDNA insert (10 ng/100 $\mu$l) was contacted with the wells of a polystyrene microtitre plate upon application of a 100% saturated NaCl solution. The resulting bound double stranded DNA was rendered single stranded by treatment with 0.2 M NaOH/0.2 mM EDTA for 5 minutes at room temperature. The prehybridisation occurred for 2 hours at 37° C. in a mixture containing 50 mM $NaHPO_4$, 5×SSC, 5×Denharts, 50% formamide, 0.1% SDS, 0.5 mM EDTA and 200 $\mu$g/ml herring sperm DNA. Hybridisation (16 hours at 37° C.) occurred in the same mixture with pGEM-FABPcDNA/100 $\mu$l labelled with digoxigenin. Rinsing took place with 1×SSC/0.1% SDS (2×5 min. at room temperature) and with either 1×SSC/0.1% SDS (2×15 min. at 40° C.), or 0.1×SSC/0.1% SDS (2×15 min. at 40° C.). The hybridized probe was detected upon application of an anti digoxigenin antibody conjugated to alkaline phosphatase. The probe also binds well to the macrobiomolecule immobilized on plastic under highly stringent hybridisation conditions such as 0.1×SSC.

In FIG. 2 DNA-DNA hybridisation is illustrated upon rinsing with different stringencies in microtitre plates. The solid line illustrates the result of 1×SSC at 40° C. and the dashed line illustrates the result of 0.1×SSC at 40° C. On the X axis the number of picograms of pGEM-FABP-cDNA probe is indicated and on the Y axis the absorption observed at 405 nm is indicated.

EXAMPLE 3
Specificity of DNA Hybridisation (After Rinsing with SSC)

Figure 3:
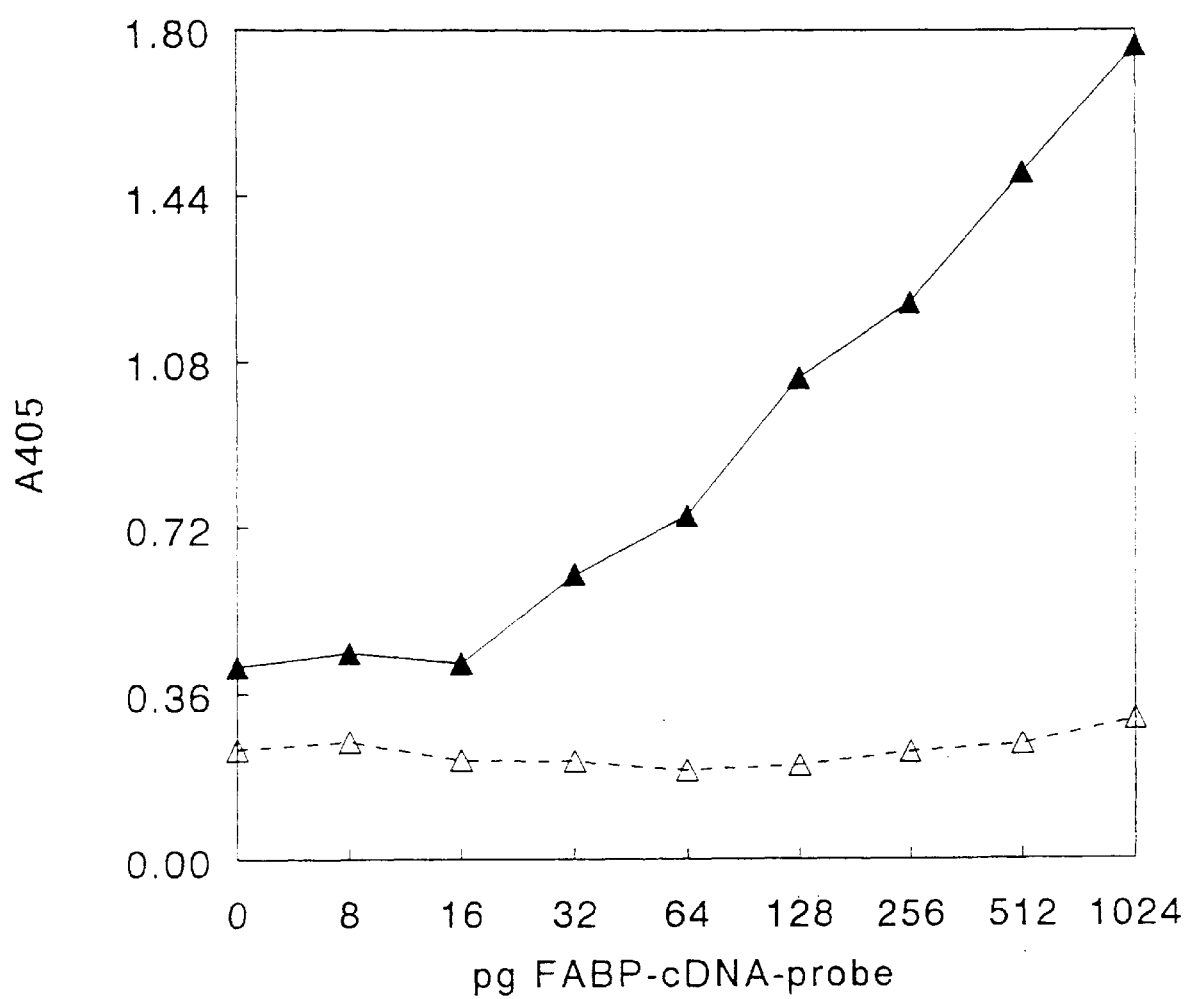

In FIG. 3 the results of this test are illustrated. pGEM vector with an FABP-cDNA insert (10 ng/100 μl) was contacted with the wells of polystyrene microtitre plates upon application of a saturated NaCl solution. The bound DNA was rendered single stranded by treatment with 0.2 M NaOH/0.2 mM EDTA. The pre-hybridisation occurred in 2 hours at 37° C. in a mixture containing 50 mM $NaHPO_4$, 5×SSC, 5×Denharts, 50% formamide, 0.1% SDS, 0.5 mM EDTA and 200 μg/ml herring sperm DNA. Hybridisation (16 hours at 37° C.) occurred in the same mixture containing the FABP-cDNA labelled with digoxygenin. Rinsing occurred with 1×SSC/0.1% SDS (2×5 min. at 22° C.) and 1×SSC/0.1% SDS (2×15 min., 40° C.) followed by 0.1×SSC/0.1% SDS (2×15 min. at 40° C.). The hybridized probe was detected by application of alkaline phosphatase conjugated to anti-digoxigenin antibody. The vector with insert was the only one to provide a positive signal. The separate vector provided a negative signal. The test is therefore specific.

Along the X axis in the figure the number of picograms of FABP-cDNA-probe has been illustrated and along the Y axis the absorption at 405 nm. The solid line with dark triangles indicates the results for coating with pGEM/FABP-cDNA. The dashed line with light triangles indicates the results for coating with pGEM.

EXAMPLE 4
Specificity of Hybridisation of DNA (After Rinsing with SDS)

The pGEM vector with FABP-cDNA insert (10 ng/100 μl) was contacted with the microtitre wells of a plastic microtitre plate upon application of saturated NaCl. The bound DNA was rendered single stranded by treatment for 5 minutes at room temperature with 0.2 M NaOH/0.2 mM EDTA. Prehybridisation occurred in 6 hours at 37° C. in 0.5 M $NaHPO_4$ at pH 7.2 which solution contained 1 mM EDTA and 7% SDS. Hybridisation (and 16 hours at 37° C.) occurred in the same solution containing digoxygenin labelled FABP-cDNA probe. Rinsing occurred in 40 mM $NaHPO_4$ (pH 7.0) plus 1 mM EDTA, which solution contained 5% SDS (4×5 min.) following by rinsing with the same solution containing 1% SDS (3×5 min.). Bound probe was detected upon application of antidigoxygenin antibody conjugated to alkaline phosphatase. The vector with insert was the only one to provide a positive signal. The separate vector provided a negative signal. The test is therefore specific.

Figure 4:
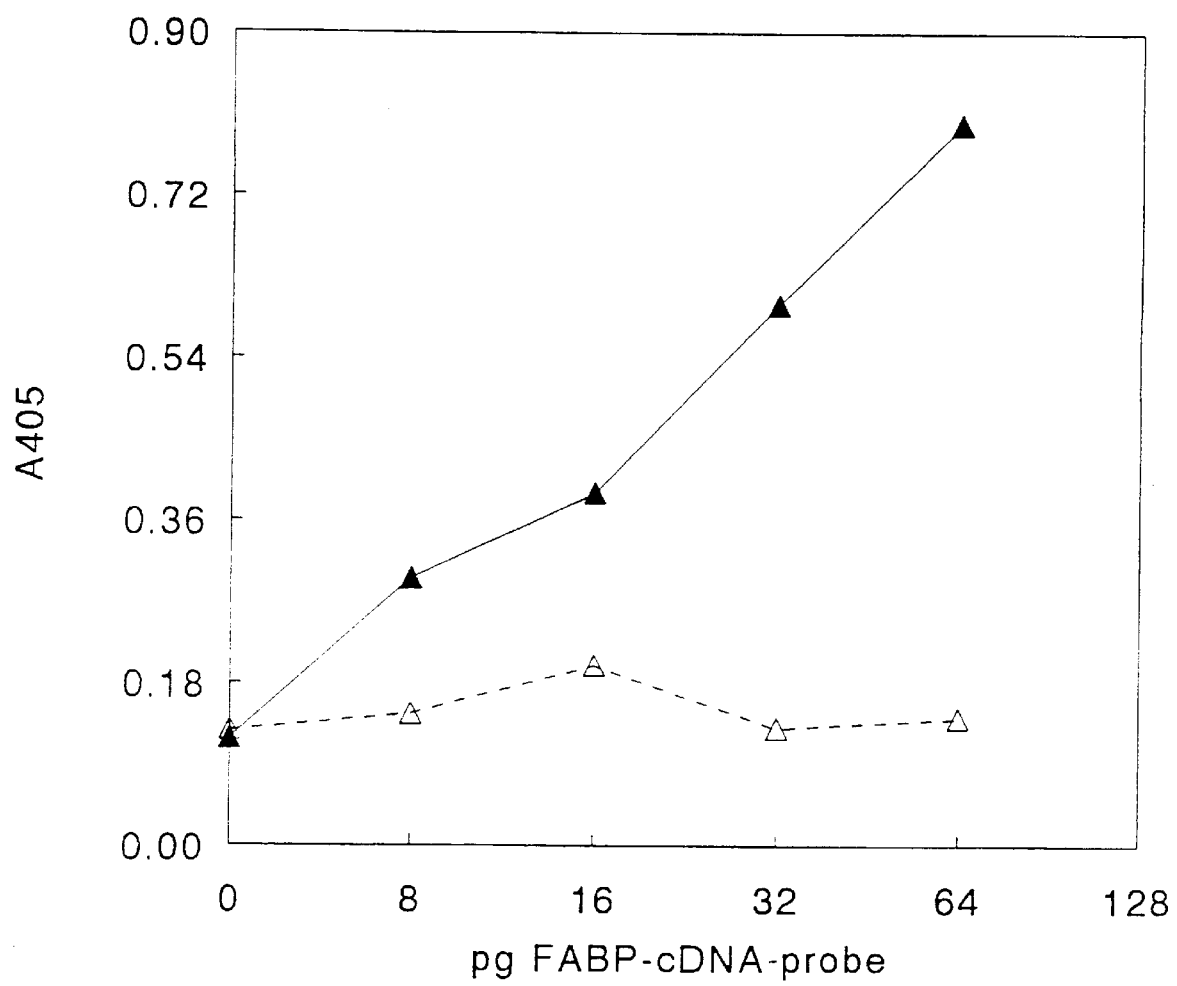

In FIG. 4 the specificity of DNA-DNA hybridisation in microtitre plates after rinsing with SDS is demonstrated. Along the X axis the number of pg FABP-cDNA probe is indicated and along the X axis the absorption is indicated as observed at 405 nm. The solid line with dark triangles indicated the coating with pGEM/FABP and the dashed line with light triangles indicates the coating with pGEM.

EXAMPLE 5
Detection of Anti DNA Antibodies in a Patient with Systemic Lupus Erythematosis.

Figure 5:
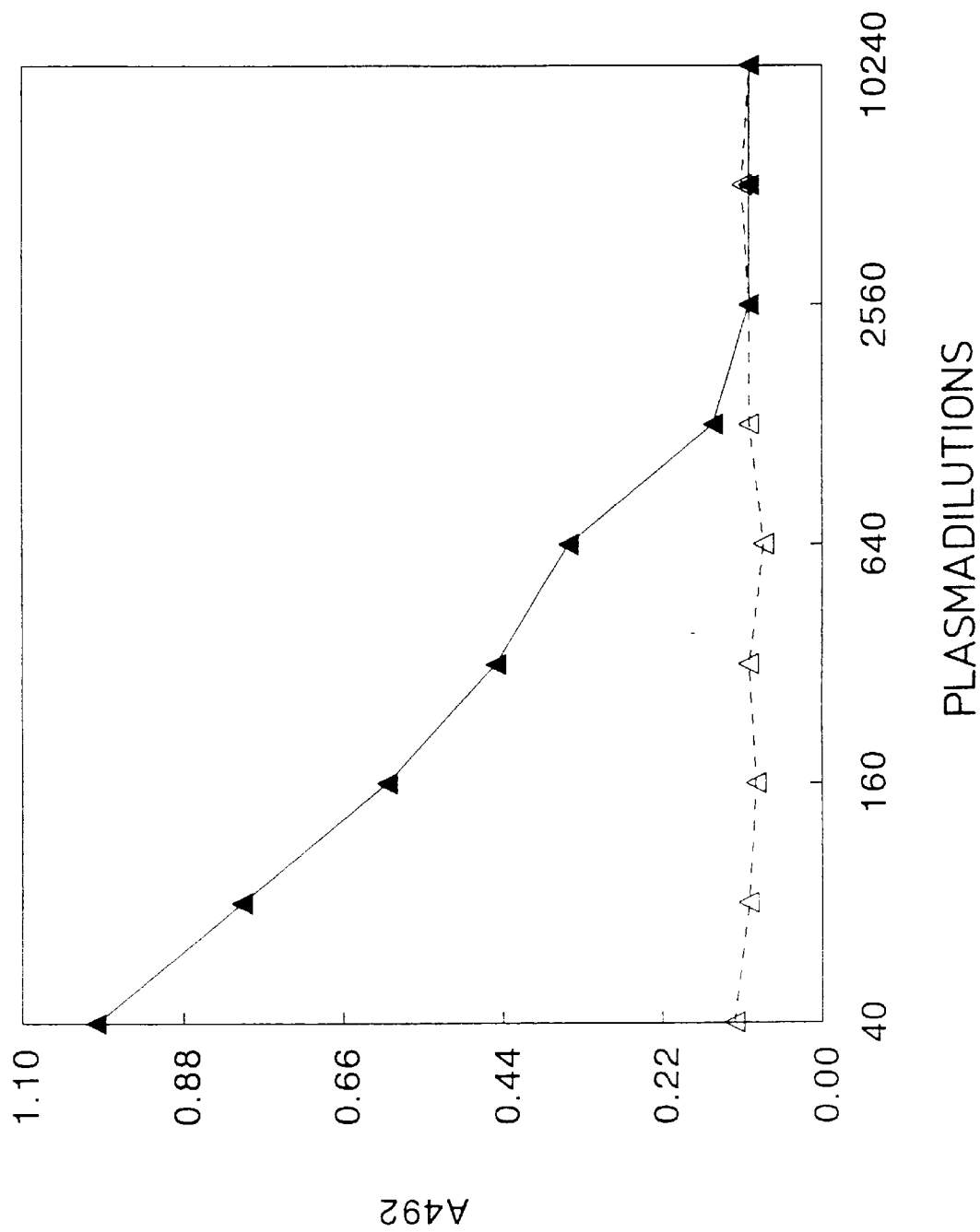

The results of this test are indicated in FIG. 5. Calfthymus DNA (1 μg/100 μl) was incubated in microtitre well upon application of a saturated NaCl solution. The incubation occurred for 16 hours at 4° C. Blood plasma was added and anti DNA antibodies were detected upon application of anti human IgG antibodies conjugated to peroxidase. Pooled plasma samples of normal blood donors were applied as control. The absorption of control plasma at A405 is even low at low dilution.

The results are indicated in FIG. 5 for anti-DNA antibodies for human plasma against Systemic Lupus Erythematosis. The X-axis indicates the plasma dilutions and along the Y axis A492 is indicated. The solid line with dark triangles indicates the result for SLE and the dashed line with light triangles indicates the control.

EXAMPLE 6
Quantification of Heparan Sulphate Upon Application of an Inhibition Enzyme Immuno Test.

Figure 6:
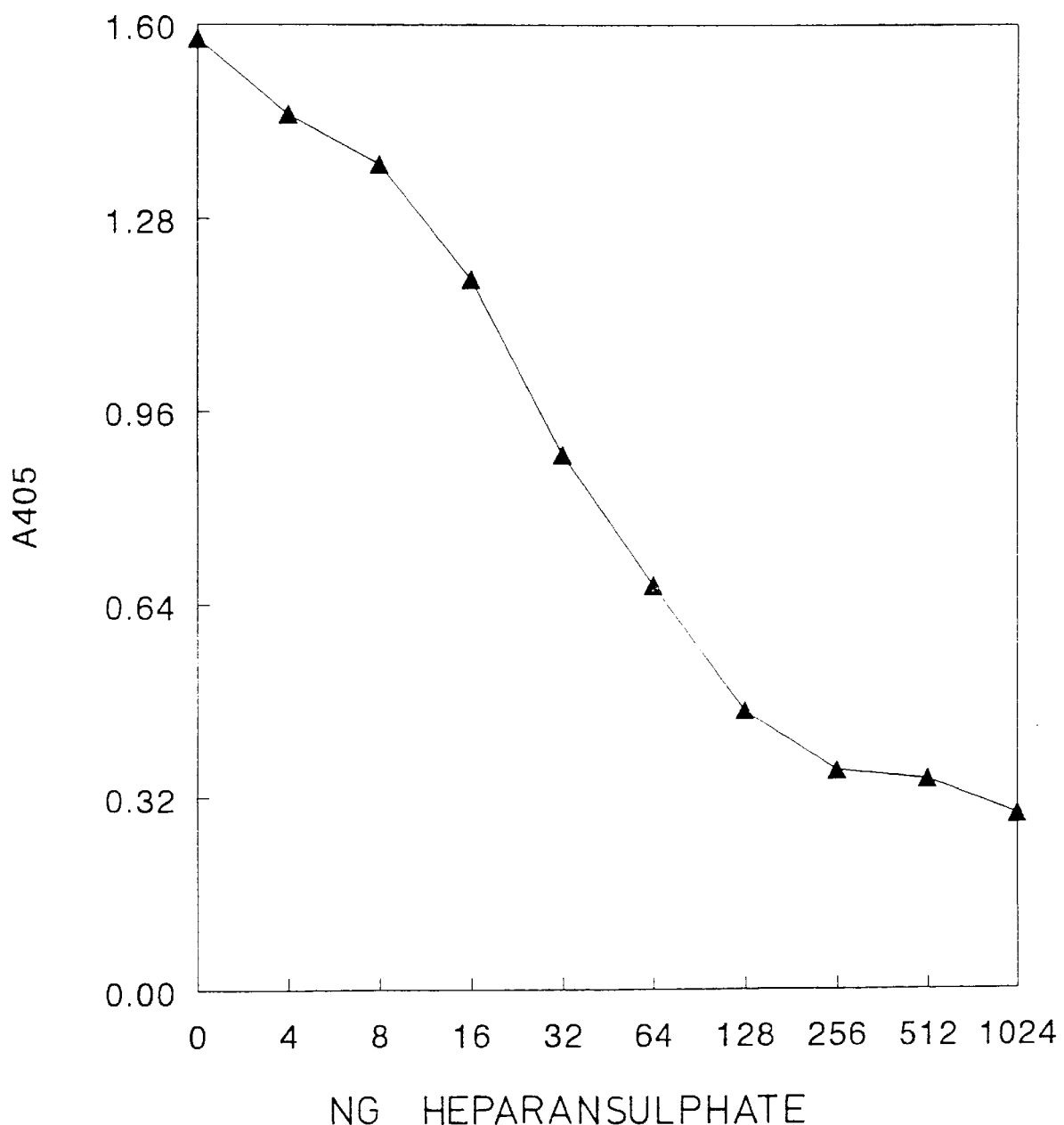

In FIG. 6 the results of this tests are illustrated. Heparan sulphate (1 μg/100 μl) was contacted with microtitre wells in a solution of 1 M HCl and 100% saturation with NaCl. The linkage step was carried out for 2 days at 4° C. The heparan sulphate to be quantified was incubated for 16 hours with mouse antiheparan sulphate antibodies at 4° C. This mixture was subsequently transferred to wells coated with heparan sulphate according to the subject method in order to let free antibody bind to the bound heparan sulphate. Bound antibody was detected upon application of anti mouse IgG antibodies which were conjugated to alkaline phosphatase. Upon application of a solution of 1 μg heparan sulphate per 100 μl the decrease in concentration of the solution can be so small as a result of the small amount of heparan sulphate that binds (probably of the order of some nanograms) that a solution already used for coating can be used a number of times to coat other plates. The detection limit for this test lies at approximately 10 ng heparan sulphate.

The quantification of heparan sulphate in inhibition immunoassay is indicated in FIG. 6. The number of ng heparan sulphate is indicated along the X axis and the absorption measured at 405 nm is indicated along the Y axis.

EXAMPLE 7
The Temperature Dependency of Coating

Heparan sulphate (0–1 μg/100 μl) was used to coat microtitre plates. A solution in saturated $(NH_4)_2SO_4$ was used for 1 hour at various temperatures. Heparan sulphate was detected by anti-heparan sulphate antibodies that were made visible upon application of anti-mouse Ig antibodies conjugated to alkaline phosphatase. Alkaline phosphatase was detected by means of incubation for 30 minutes at 22° C. with p-nitrophenyl phosphate. The higher the temperature the more heparan sulphate was bound.

Figure 7:
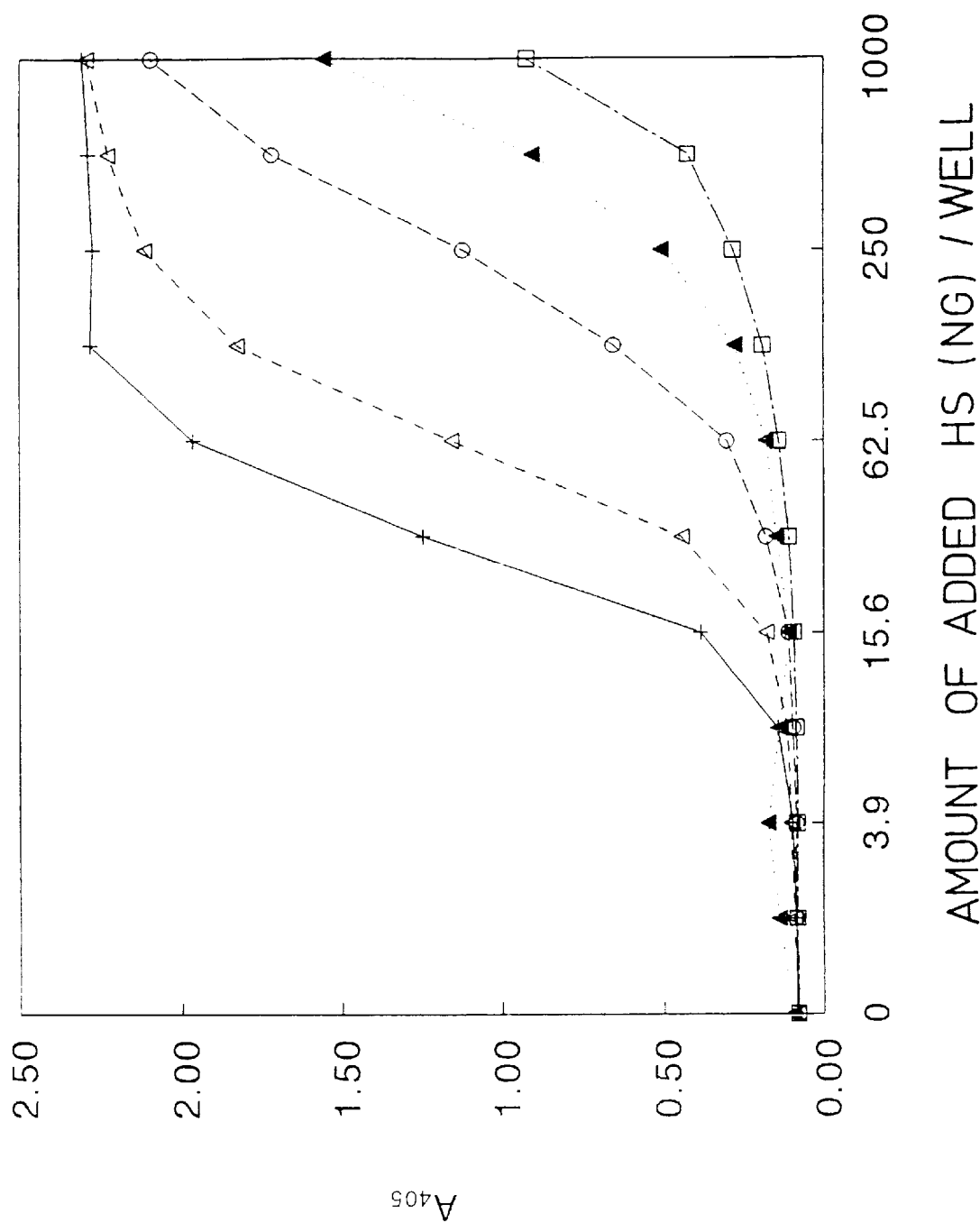
Figure 6:
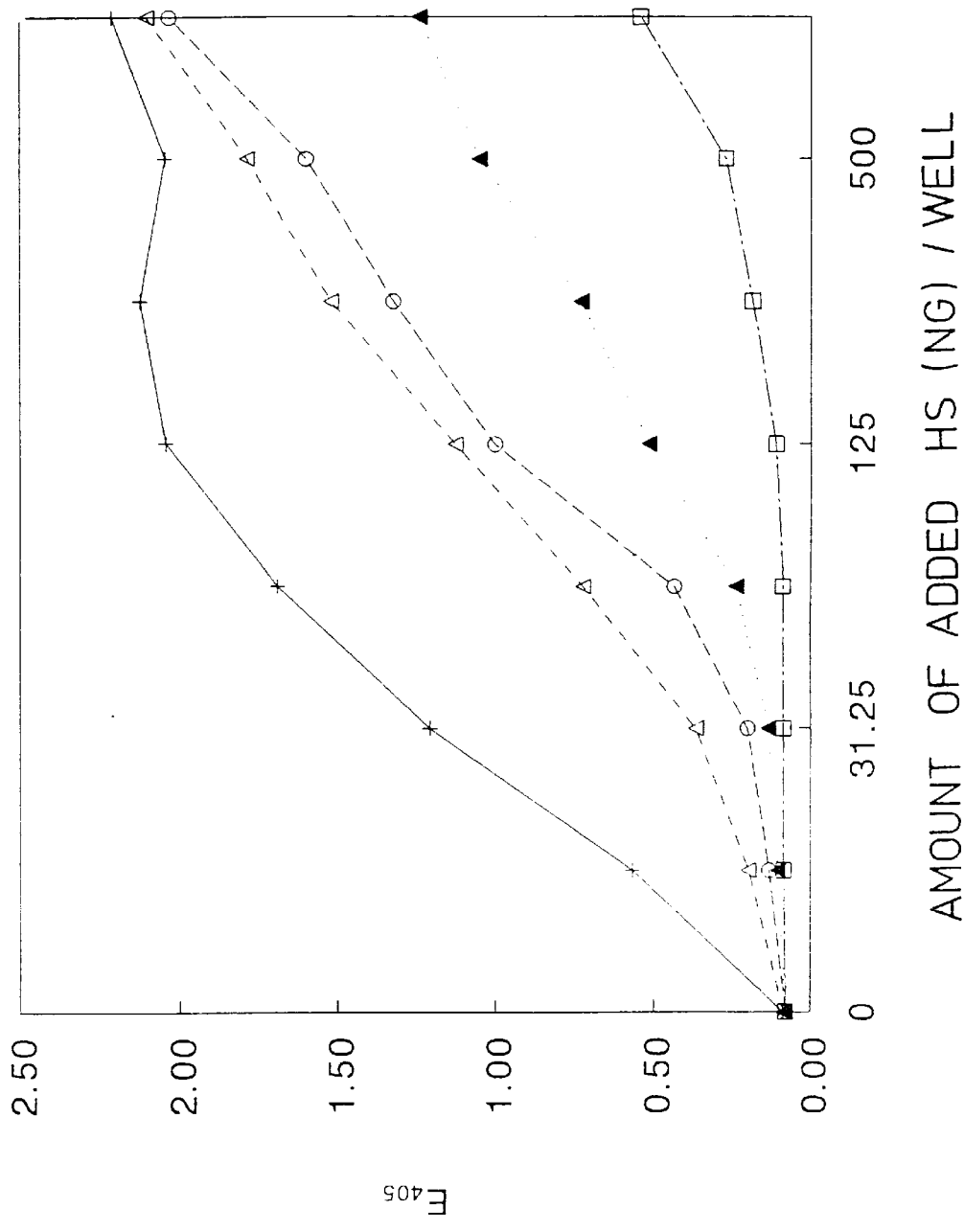

The solid line in FIG. 7 illustrates the result at 80° C. The dashed line with light triangles illustrates the result at 56° C. The dashed line with light circles illustrates the result at 37° C. The dotted line with dark triangles illustrates the result at 25° C. and the dashed line with light squares illustrates the result at 4° C. The amount of heparan sulphate in ng added per well is indicated along the X axis. Along the Y axis the absorption at 405 nm is illustrated. FIG. 5 clearly illustrates the temperature dependency of coating.

EXAMPLE 8
Temperature Dependency of Coating

Heparan sulphate (0–62.5 ng/100 μl) was used to coat microtitre wells whereby a saturated $(NH_4)_2SO_4$ solution was used for 1 hour at various temperatures. Heparan sulphate was detected by antiheparan sulphate antibodies made visible upon application of anti-mouse Ig antibodies conjugated to alkaline phosphatase. Alkaline phosphatase was detected by incubation with p nitro phenyl phosphate for 16 hours at 4° C. Coating with a concentration of 10 mg heparan sulphate/100 μl is sufficient to obtain a strong signal, an absorption of approximately 1. Binding does not occur in $H_2O$ and in salt solution buffered with phosphate (0.05 M sodium phosphate buffer (pH 7.4)+0.15 M NaCl).

In FIG. 8 the temperature dependency of coating is also illustrated. The solid line provides the values obtained at 80° C. and $(NH_4)_2SO_4$, the dashed line with a dark dot indicates the values at 80° C. with PBS and the alternately dashed line with dark dots provides the results at 80° C. and with $H_2O$. The solid line with a light triangle illustrates the results at 4° C. with $(NH_4)_2SO_4$, the dashed line with light triangle the result at 4° C. with PBS and the alternately dashed line with light triangle provides the result at 4° C. with $H_2O$. Along the X axis the amount of HS added in ng/well is indicated and along the Y axis the absorption at 405 nm is indicated.

EXAMPLE 9

Time Dependency of Coating

Heparan sulphate (0–1 µg/100 µl) was used to coat microtitre wells, wherein a solution of saturated $(NH_4)_2SO_4$ was used for 1 hour at 25° C. Heparan sulphate was detected by anti-heparan sulphate antibodies made visible upon application of anti-mouse Ig antibodies conjugated to alkaline phosphatase. Alkaline phosphatase was detected by incubation with p nitrophenyl phosphate for 1 hour at 22° C. The amount of bound heparan sulphate bound is positively correlated to the length of time of incubation. In FIG. 9 the result after 16 hours is illustrated by a solid line, after 6 hours by a dashed line with a light triangle, after three hours by a dashed line with a light circle, after 1 hour with a dotted line with dark triangle and after 10 minutes of incubation by an alternately dashed line with a light square. The amount of heparan sulphate (ng) added per well is indicated along the X axis whereas the adsorption at 405 nm is indicated along the Y axis. The test was carried out at 22° C.

What is claimed is:

1. A method for linking a non-proteinaceous, negatively charged nucleic acid or glycosaminoglycan macrobiomolecule to a plastic without use of a spacer molecule or activation of the plastic, which comprises:

(a) contacting the macrobiomolecule and the plastic with a non chaotropic solution containing a salt in an amount of at least 20% of its saturation concentration, and/or having a pH below the pKa of the charged groups of the macrobiomolecule to be linked, to remove the water coat of the macrobiomolecule or shield the negatively charged groups thereof and form a direct link between the macrobiomolecule and the plastic; and (b) removing the solution.

2. The method of claim 1, wherein the macrobiomolecule is a single stranded deoxyribonucleic acid (DNA) molecule, a double stranded deoxyribonucleic acid (DNA) molecule or a ribonucleic acid (RNA) molecule.

3. The method of claim 1, wherein the macrobiomolecule is contacted in step (a) with a solution containing a non chaotropic salt of the Hofmeister series of salts or a salt of a metal selected from Groups I and II of the Periodic Table of Elements in an amount of at least 50% of its saturation concentration.

4. The method of claim 3, wherein the salt contains a chloride, bromide, phosphate, sulphate or acetate anion.

5. The method of claim 4, wherein the salt comprises a chloride.

6. The method of claim 4, wherein the salt is at least one of the salts NaCl, KCl, LiCl, $MgCl_2$, $MgSO_4$, $(NH_4)_2SO_4$, $NaH_2PO_4$ or $Ca(Ac)_2$.

7. The method of claim 4, wherein the salt is ammonium sulfate.

8. The method of claim 3, wherein the salt is incorporated in the solution in an amount of from 70% to 100% of saturation.

9. The method of claim 3, wherein the linking is carried out at a temperature between 0° and 100° C.

10. The method of claim 9, wherein the linking is carried out at a temperature between 4° and 80° C. and over a period varying from overnight to 5 minutes.

11. The method of claim 9, wherein the solution is removed in step (b) by rinsing with water or a salt solution buffered with Tris and Tween 20.

12. The method of claim 1, wherein the macrobiomolecule is contacted in step (a) with a solution having a pH lower than the pKa of the charged groups of the macrobiomolecule to be linked.

13. The method of claim 12, wherein the linking is carried out at a temperature between 0° C. and 100° C.

14. The method of claim 12, wherein the linking is carried out at a temperature between 4° C. and 80° C. and over a period varying from overnight to 5 minutes.

15. The method of claim 12, wherein the solution is removed in step (b) by rinsing with water or a salt solution buffered with Tris and Tween 20.

16. The method of claim 1, wherein the plastic is a solid carrier to be coated with the macrobiomolecule and is constituted of polystyrene, polyethylene, polyvinylidene difluoride or polycarbonate.

17. The method of claim 16, wherein the carrier is a microtitre plate well.

18. The method of claim 1 for linking a glycosaminoglycan macrobiomolecule to a plastic wherein the macrobiomolecule and the plastic are contacted in step (a) with a substantially saturated solution of a non chaotropic salt at an acid pH.

19. The method of claim 1 for linking single stranded DNA to a plastic, wherein double stranded DNA is contacted with the plastic in step (a) and the linked DNA is subsequently rendered single stranded.

20. The method of claim 19, wherein contact step (a) is carried out in a saturated salt solution in water.

21. The method of claim 19, wherein the double stranded DNA is rendered single stranded, after the removal step (b), by the addition of 0.2M NaOH/0.2M EDTA thereto.

22. A microtitre plate having plastic wells directly coated with a negatively charged non-proteinaceous nucleic acid or glycosaminoglycan macrobiomolecule without the use of a spacer molecule, prepared by:

(a) contacting the macrobiomolecule and the plastic with a non chaotropic solution containing a salt in an amount of at least 20% of its saturation concentration, and/or having a pH below the pKa of the charged groups of the macrobiomolecule to be linked, to remove the water coat of the macrobiomolecule or shield the negatively charged groups thereof and form a direct link between the macrobiomolecule and the plastic; and (b) removing the solution.

23. The microtitre plate of claim 22, wherein the plastic wells of the plate are constituted of polystyrene, polyethylene, polyvinylidene difluoride or polycarbonate.

24. A test kit, comprising a non-proteinaceous, negatively charged nucleic acid or glycosaminoglycan macrobiomolecule directly linked to plastic without the use of a spacer molecule, wherein the macrobiomolecule is coated on the plastic by:

(a) contacting the macrobiomolecule and the plastic with a non chaotropic solution containing a salt in an amount of at least 20% of its saturation concentration, and/or having a pH below the pKa of the charged groups of the macrobiomolecule to be linked, to remove the water coat of the macrobiomolecule or shield the negatively charged groups thereof and form a direct link between the macrobiomolecule and the plastic; and (b) removing the solution.

* * * * *